(12) United States Patent
Claypool et al.

(10) Patent No.: US 7,819,876 B2
(45) Date of Patent: Oct. 26, 2010

(54) ORTHOPAEDIC PIN DRIVER (75) Inventors: Jody L. Claypool, Columbia City, IN (US); Maleata Y. Hall, Warsaw, IN (US); Kathy J. Radford, Winona Lake, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 1071 days.

(21) Appl. No.: 11/257,564

(22) Filed: Oct. 25, 2005

(65) Prior Publication Data
US 2007/0123894 A1 May 31, 2007

(51) Int. Cl.
*A61B 17/00* (2006.01)

(52) U.S. Cl. .......................... 606/85; 606/86 R; 606/84; 606/79

(58) Field of Classification Search .................. 606/79, 606/80, 81, 82, 83, 84, 85, 116, 86 R, 86 A, 606/105, 176, 178, 172, 184, 185; 269/266; 600/424, 592; 81/185; 604/173, 102, 104; 407/20, 21, 22, 23, 24, 25, 26, 27, 28, 29, 407/29.1, 29.11, 29.12, 29.13, 29.14, 29.15; 227/142, 143, 2, 3, 5, 66, 76
See application file for complete search history.

(56) References Cited

U.S. PATENT DOCUMENTS

| 3,023,485 | A | * | 3/1962 | Barthod | 29/81.14 |
| 3,223,182 | A | * | 12/1965 | Mikiya | 173/114 |
| 3,698,267 | A | * | 10/1972 | Denney | 81/185 |
| 4,142,517 | A | | 3/1979 | Contreras | |
| 4,594,759 | A | * | 6/1986 | Ikeda | 29/81.16 |
| 4,684,113 | A | * | 8/1987 | Douglas et al. | 269/21 |
| 5,267,382 | A | * | 12/1993 | Aulson et al. | 29/81.14 |
| 5,417,683 | A | * | 5/1995 | Shiao | 606/1 |
| 5,586,607 | A | * | 12/1996 | Neumaier et al. | 173/117 |
| 5,667,509 | A | | 9/1997 | Westin | |
| 5,738,345 | A | * | 4/1998 | Schroeder et al. | 269/266 |
| 5,846,464 | A | | 12/1998 | Hoffman | 264/219 |
| 6,152,245 | A | * | 11/2000 | Nilsson | 173/218 |
| 6,264,211 | B1 | * | 7/2001 | Granado | 279/143 |
| 6,588,301 | B1 | | 7/2003 | Chanet | |
| 6,689,103 | B1 | | 2/2004 | Palasis | |
| 6,764,452 | B1 | | 7/2004 | Gillespie | |
| 6,824,552 | B2 | | 11/2004 | Robison | |
| 6,843,796 | B2 | | 1/2005 | Harari | |
| 7,125,010 | B2 | * | 10/2006 | Moore et al. | 269/266 |
| 2002/0083598 | A1 | * | 7/2002 | Julien | 30/350 |
| 2004/0147932 | A1 | | 7/2004 | Burkinshaw | |
| 2007/0156066 | A1 | * | 7/2007 | McGinley et al. | 600/587 |

* cited by examiner

*Primary Examiner*—Eduardo C Robert
*Assistant Examiner*—Jan Christopher Merene
(74) *Attorney, Agent, or Firm*—Baker & Daniels LLP

(57) ABSTRACT

An orthopaedic pin driver is presented for impacting bone during a surgical procedure.

38 Claims, 4 Drawing Sheets

ORTHOPAEDIC PIN DRIVER

FIELD OF THE INVENTION

The present invention relates to instruments for use in orthopaedic procedures. More particularly, the present invention relates to instruments used to remove and/or abrade bone during a surgical procedure.

Orthopaedic surgical procedures exist to treat a wide variety of conditions of the bones and joints of the human body. For example, procedures exist to remove damaged or diseased tissues such as bone tumors, lesions, and other defects and allowing the remaining tissue to heal. Procedures also exist to replace damaged or diseased tissues such as joint replacement surgery. Degenerative and traumatic damage to the articular cartilage of skeletal joints can result in pain and restricted motion. Prosthetic joint replacement is frequently utilized to alleviate the pain and restore joint function. In such a procedure, an incision is made to expose the bones comprising the joint. Cutting guides are then used to guide saw blades, burrs, drills, reamers, and other bone removal instruments to remove the articular surfaces that are to be replaced.

For example, in a typical knee replacement surgery, femoral cut guides are used to guide a saw blade to make bone cuts to prepare the femur to receive a prosthetic femoral implant. Similarly, tibial resection guides are used to guide cuts on the proximal tibia. Joint replacement surgery at other joints in the body also uses various guides and bone removal tools to prepare the bones to receive the implants.

Many surgical procedures are now performed with surgical navigation systems in which sensors detect tracking elements attached in known relationship to an object in the surgical suite such as a surgical instrument, implant, or patient body part. The sensor information is fed to a computer that then triangulates the three dimensional position of the tracking elements within the surgical navigation system coordinate system. The computer can resolve the position and orientation of the object and display the position and orientation for surgeon guidance. For example, the position and orientation can be shown superimposed on an image of the patient's anatomy obtained via X-ray, CT scan, ultrasound, or other imaging technology.

SUMMARY

The present invention provides an orthopaedic pin driver for impacting bone during a surgical procedure.

In one aspect of the invention, an orthopaedic pin driver for impacting bone at a surgical site includes a housing having a proximal end, a distal end, and a longitudinal axis therebetween. An array of pins is mounted in the housing for reciprocating motion parallel to the longitudinal axis between a first longitudinal position and a second longitudinal position. Each pin has a proximal end and a distal end. The proximal end of each pin projects from the housing at least when each pin is in the second longitudinal position. A drive mechanism engages the pins to reciprocate the pins between the first and second positions.

In another aspect of the invention, the pin driver further includes a limiter engaging at least one pin. The limiter is controllable to limit the pin's projection distance.

In another aspect of the invention, the pin driver further includes a surgical navigation system including a surgical navigation coordinate system. The surgical navigation system is able to output a control signal to control the drive mechanism. A tracking element is mounted to the housing and is detectable by the surgical navigation system to indicate the position of the pins within the surgical navigation system. The surgical navigation system is able to control the drive mechanism to reciprocate the pins when the pins are positioned in a desired relationship to the bone.

In another aspect of the invention, a method of removing a portion of a bone at a surgical site includes the steps of: first, providing an orthopaedic pin driver comprising an array of pins mounted for reciprocation within a housing, a drive mechanism being coupled to the pins to reciprocate the pins with the housing; second, positioning the pin driver adjacent to the bone; and third, driving the array of pins to impact the bone.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Embodiments of an orthopaedic pin driver according to the present invention are useful to impact bone during surgical procedures throughout the body to compact, mark, remove, and/or otherwise modify the bone. For example, total knee joint replacement surgery has been used to illustrate the pin driver. However, the pin driver is also useful to impact bone adjacent joints of the hip, shoulder, ankle, elbow, wrist, the digits of the hands and feet, vertebral bodies, and/or other joints. The pin driver is also useful to impact bone at locations spaced from the joints such as to remove tumors, lesions, and other defects, and/or where it is desirable to roughen bone or produce bleeding bone to facilitate fixation and/or speed healing. For example, it may be desirable to roughen bone to facilitate the interdigitation of bone cement with the bone. The pin driver may also be used to compact bone into a more dense form such as to prepare a substrate for seating an implant. The pin driver may also be used to mark bone such as to produce a line, dot, and/or other recognizable mark for later reference in a surgical procedure.

Embodiments of a pin driver include one or more pins driven in a reciprocating piston-like fashion to impact a bone. As the pin impacts the bone, it fractures and/or punctures the bone. Depending on the spacing of the impact sites, the bone surface may be perforated, roughened, or pulverized. With closely spaced impact sites, the bone surface may be pulverized such that it may be suctioned and/or scraped away to remove an area of bone. The pins may vary in size depending on the application and the desired impact size. However, smaller and/or sharper pins will tend to puncture hard bone more easily. To further facilitate the action of the pins, they may be sharpened to a conical point, chisel point, and/or other suitable tip geometry. They may also be solid or hollow. Hollow tipped pins may present sharp cutting rims as well as permit irrigation and/or aspiration through the pins. For example, the pins may be in the form of hollow tubes with sharpened chisel-shaped tips similar to a hypodermic needle.

Where a plurality of pins is provided, they may be arranged in an array of rows and columns. The pins may all move at once or they may be driven selectively. The pins may be arranged in a pattern corresponding to a pattern to be produced on the bone such as a rectangle, "X"-shape, or other desired shape. The pins may be arranged in a general array, such as a rectangular or circular array, but selectively driven to produce other patterns such as an "X"-shape, smaller rectangle, smaller circle, and/or other desired shape.

The pins may be made of plastic, ceramic, metal, and/or other suitable materials. For example, the pins may be made of stainless steel. A housing for the pin driver may be made of plastic, ceramic, metal, and/or other suitable materials. For example, the housing may be made of a polymer such as polyaryletherketone.

The pins may be driven by linear actuators, stepper motors, electromagnetic coils, shape memory alloys, and/or other suitable drive mechanism. The pins may fire with the same force and projection distance each time they fire or they may be fired with varying force and/or projection distance. The force and projection distance may be varied by varying the signal sent to the drive mechanism. With some drive mechanisms, varying the signal may vary the inertia of the drive mechanism and pins to vary the force and projection distance. For example, the pins may be driven by hammers that move the pins under the influence of electromagnets. The force and projection distance may be varied by changing the signal sent to the electromagnets such as by varying the signal amplitude and/or duration.

Pin projection distance may also be controlled by mechanical devices such as separately controlled pin limiters. For example, one or more mechanically controlled limiters may be formed as plates that engage a collar on one or more pins to limit pin travel. In another example, the limiters may attach directly to the pins. The pins may be controlled independently or as one or more groups of pins. The limiters may be controlled by manual actuators, powered actuators, motors, coils, shape memory alloys and/or other suitable control mechanisms. For example, the limiters may be connected to a manually controlled lever and the travel distance may be set by the user manipulating the lever. In another example, the limiters may be moved by a powered mechanism. The pins may be driven by a drive mechanism controlled by a first electrical input signal and the limiters may be moved under control of a second electrical input signal. For example, the limiters may be connected to a shape memory alloy that changes shape under control to vary the limiter position.

The pins themselves may change shape to vary pin projection distance. The pins may change length, diameter, cross-section, and/or otherwise change shape. The pins may change shape by telescoping, swelling, shrinking, twisting, bending, kinking, and/or by some other mechanism. The pins may be made of a shape memory alloy so that they may change shape under control of a second control input while they are being driven by a drive mechanism under control of a first control input. For example, the pins may be driven by electromagnets controlled by a first electrical input signal and the pin projection distance may be limited by changing the length of the pins by way of a second electrical input signal.

The shape memory alloy may change shape due to caloric, electrical, chemical, mechanical, and/or other input. For example the shape memory alloy may change length in response to an electrical current. Examples of shape memory alloys include nickel-titanium (nitinol), copper-aluminum-nickel, copper-zinc-aluminum, iron-manganese-silicon, and other suitable alloys. The shape memory alloy may be in the form of wires, pins, bars, sheets, tubes, and/or other suitable shapes.

The pin driver may include irrigation and/or aspiration conduits to facilitate removing cut and/or crushed bone. For example, the pins may be hollow to allow irrigation and/or aspiration through the pins. In another example, the instrument may include conduits adjacent the pins for irrigation and/or aspiration. Fluid may also be passed through the conduits to cool the pin driver and/or bone.

The pin driver may be positioned using a cut guide so that the pins impact the bone at a desired location, angle, and/or depth. The cut guide may be positioned in a desired orientation relative to the bone and the pin driver referenced to the cut guide to position the pin driver.

The pin driver may include one or more tracking elements detectable by a surgical navigation system to guide the positioning of the pin driver. For example, the surgical navigation system may include multiple sensors at known locations that feed tracking element position information to a computer. The computer may then use the position information from the multiple sensors to triangulate the position of the tracking element within the surgical navigation coordinate system. The tracking element may be attached to the pin driver in a known orientation such that the surgical navigation system can determine the position and orientation of the impact envelope of the pin driver by detecting the position and orientation of the tracking element and resolving the position and orientation of the impact envelope. Tracking may include resolving the position of individual pins so that the impact envelope of each pin is represented in the system. Tracking elements may be detectable by imaging, acoustically, electromagnetically, or by other suitable detection means. Furthermore, tracking elements may be active or passive. Examples of active tracking elements may include light emitting diodes in an imaging system, ultrasonic emitters in an acoustic system, and electromagnetic field emitters in an electromagnetic system. Examples of passive tracking elements may include elements with reflective surfaces.

The surgical navigation system may optionally provide position feedback such as by a computer display overlaying an image of the pin driver position with an image of the surgical anatomy. It may more simply optionally produce an audible tone and/or indicator light to signal correct positioning. The surgical navigation system may provide firing signals to the pins to cause the pins to fire only when they are in the correct position. For example, an impact zone may be defined within the surgical navigation system such that whenever the impact envelope of a pin is within the impact zone, the pin is activated. The depth and/or force of firing may be also controlled by the surgical navigation system to tailor the shape of the impact envelope to the desired impact zone.

Figures 1, 2:
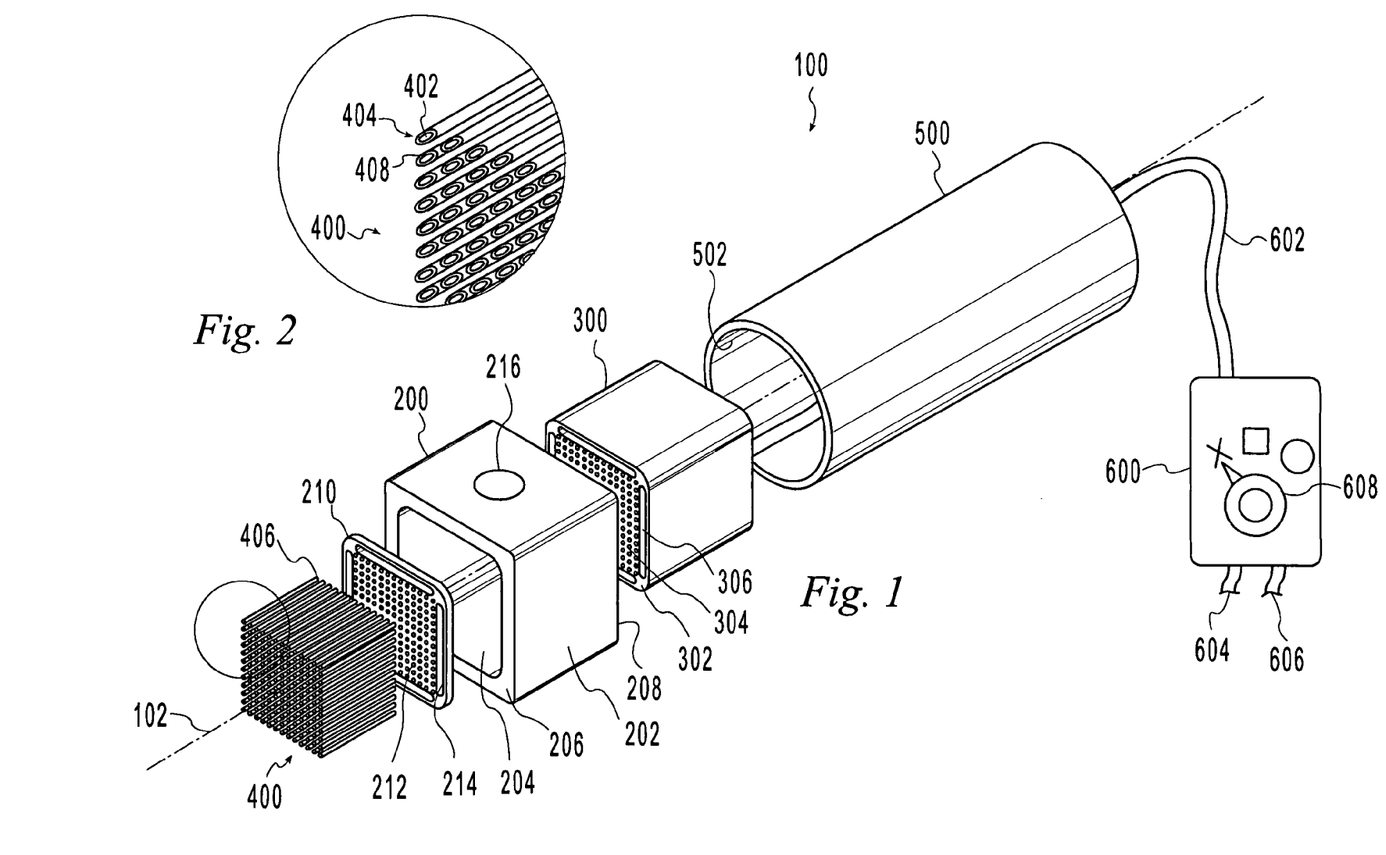
FIG. 1 is an exploded perspective view of an instrument according to the present invention.
FIG. 2 is a detailed view of a portion of FIG. 1.
Figure 3:
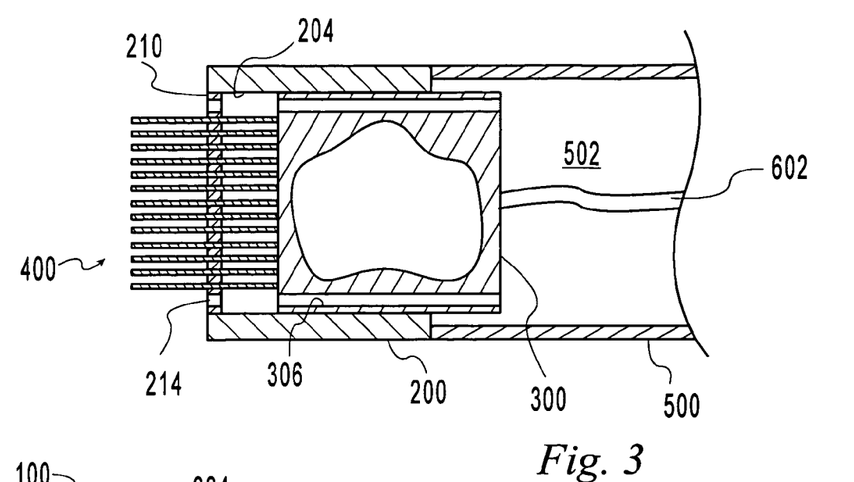
FIG. 3 is a cross-sectional view of the instrument of FIG. 1.

FIGS. 1-3 show an illustrative pin driver 100. The illustrative pin driver includes a housing 200, a drive mechanism 300, an array of pins 400, and a handle 500 arranged along a longitudinal axis 102. A control unit 600 is connected to the drive mechanism 300 to provide a control signal.

The housing 200 includes a wall 202 defining an inner cavity 204 for receiving the drive mechanism 300. The housing has a proximal end 206 oriented toward the surgical site and a distal end 208 oriented away from the surgical site. A pin guide 210, in the form of a perforated plate, is mounted in the inner cavity 204 adjacent the proximal end to receive and provide longitudinal support to the array of pins 400. The pins 400 slide longitudinally within the openings 212 in the pin guide. The drive mechanism 300 includes a perforated proximal face 302. The holes 304 in the proximal face 302 also receive and support the pins 400 in longitudinal sliding relationship. The illustrative pin driver includes irrigation/aspiration conduits 214, 306 that permit fluid to be conducted into the surgical site and/or debris to be suctioned away from the surgical site to facilitate removal of cut and/or crushed bone. The conduits may also conduct cooling fluid to cool the pin driver and/or bone. The illustrative conduits 214, 306 are in the form of elongated slots extending longitudinally through the pin guide 210 and drive mechanism 300 proximal to distally parallel to each of the housing sides and surrounding the pins 400. The handle 500 is mounted to the housing 200 and includes a hollow interior 502 through which irrigation and/or aspiration can be conducted.

In the illustrative pin driver 100, the pins 400 are in the form of hollow cylinders having a longitudinal bore 402 that permits irrigation and aspiration through the pins. The proximal ends 404 of the pins 400 are formed as sharpened chisel-shaped tips similar to hypodermic needles. The illustrative pins 400 present a sharp cutting rim 408 to facilitate bone cutting.

The control unit 600 produces the signals required to drive the pins 400 in the desired manner. The control unit 600 may be located in the pin driver 100, for example in the drive mechanism 300, or it may be a separate component connected to the drive mechanism by a cable 602 as shown. The illustrative control unit 600 also includes a power cable 604 that provides power to the pin driver 100 and an optional data cable 606 that may be used to connect the control unit 600 to a source for control information such as a computer in a surgical navigation system.

The control unit 600 may be activated to drive the pins 400 in a continuous motion to provide a simple bone abrasion mode. The pins may all fire at once or they may be driven to fire in a predetermined sequence. Continuous firing is useful for roughening bone to enhance cement fixation, creating bleeding bone to promote healing, compacting bone, and/or other applications where simple bone abrasion is desired. The pin driver 100 may be held in a specified orientation adjacent the bone by placing it against or within a cut guide as is known in the art for guiding saw blades and then activating the pin driver. The pin driver 100 may be used to remove the bone surface by activating it adjacent a bone and then suctioning, washing, scraping, and/or otherwise removing the crushed bone. The pin driver 100 may be repeatedly applied to remove a layer at a time to a desired depth. The pins 400 may be provided in a specific shape to produce a desired shape on a bone. For example, an "X"-shaped array of pins may be provided to produce an "X"-shaped depression in a bone to receive an "X"-shaped fixation stem. Likewise, the pins 400 may be provided in a general array, as shown, but be selectively driven to produce a desired shape. The control unit 600 may include pre-programmed pin driving signals to produce different shapes. The user then only need select the desired shape, for example by turning a selector dial 608, and the pins corresponding to that shape will be driven by the control unit.

The exemplary pin driver 100 further includes a tracking element 216 mounted on the housing 200. The tracking element may be a single element or an array of elements trackable by a surgical navigation system. In the illustrative example, the tracking element 216 is a coil detectable by the surgical navigation system enabling the system to resolve the position and orientation of the pin driver 100. The geometry of the pin driver 100 is defined within the surgical navigation system such that the position of the pins 400 can be resolved and an impact envelope defined within the system. By driving the pins 400 known distances with known timings, the instantaneous impact envelope of each pin 400 can also be resolved. The surgical navigation system may provide feedback to the user indicating the position of the impact envelope relative to a patient body part.

Alternatively, or in addition to providing position feedback to the user, the surgical navigation system may directly interface with the control unit 600. By interfacing the control unit 600 with the surgical navigation system via cable 606, location dependent drive inputs to the pins 400 may be provided. For example, a particular area within the surgical site may be identified within the surgical navigation system coordinate system as an impact zone and/or another area may be identified within the surgical navigation system coordinate system as a no-impact zone. Thus, with the surgical navigation system activated, the pins 400 may be driven to resect tissue at the surgical site. If the impact envelope of the pins begins to exit an impact zone and/or enter a no-impact zone, a signal from the surgical navigation system to the control unit 600 may cause one or more pins to stop firing. Thus, the pin driver 100 can be manually manipulated within the surgical site and the pins 400 will only resect tissue when the impact envelope of the pins 400 is within a predefined area to be resected. The precise location of the pins 400 may be unknown to the surgeon. However, the surgeon can manipulate the pin driver 100 with confidence knowing that it will only be driven to resect tissue when it is in the predefined impact zone.

Figures 4, 5:
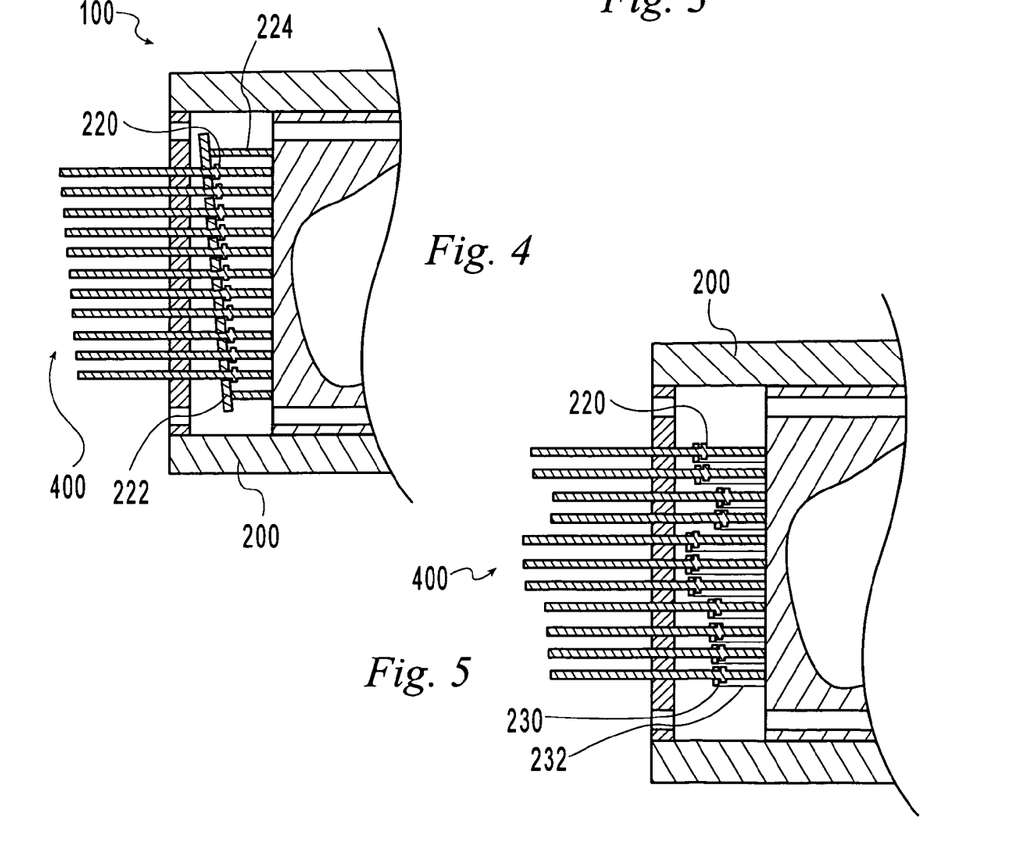
FIGS. 4 and 5 are detailed cross-sectional views of the instrument of FIG. 1 showing alternative depth limiting mechanisms.

FIGS. 4 and 5 illustrate optional mechanisms for limiting pin travel and consequently the projection distance of the pins 400 from the housing 200. In FIG. 4, each pin 400 includes an enlarged annular collar 220 extending radially from the pin shaft. A limiter plate 222 contains a plurality of holes that receive the pins 400 in sliding relationship. One or more links 224 connect the limiter plate 222 to the housing. In the illustrative pin driver 100, the limiter plate 222 defines a planar square corresponding to the illustrative pin configuration and a link 224 joins each corner of the limiter plate 222 to the drive mechanism 300. The links 224 move the limiter plate 222 to reposition it relative to the pins 400. As the pins 400 are driven, the collars 220 abut the limiter plate 222 to limit the travel of the pins 400. The links 224 can be controlled to position the limiter plate 222 at a variety of longitudinal positions and orientations relative to the housing 200 to control the projection distance of the pins 400. By angling the limiter plate 224, an angled pin 400 projection pattern is produced as shown. A flexible limiter plate 222 could be curved into a variety of shapes by the links 224 to produce corresponding curved pin 400 projection patterns. The links can be controlled by manually actuating a knob, lever, slide, and/or other mechanism. For example, one or more levers (not shown) can be mounted on the housing 200 and connected to the links 224 such that movement of the one or more levers results in movement of the limiter plate 222. In the illustrative mechanism, the links 224 are made of a shape memory alloy and each link is connected to an electrical circuit such that an electrical current can be sent to the link to cause the link to change length. The current to each link is controlled by a second control signal from the surgical navigation system, separate from the first control signal that drives the pins, to produce a desired limit to pin travel.

The mechanism of FIG. 5 is similar to that of FIG. 4 except that individual limiters 230 are provided for each pin 400 in the form of a ring encircling each pin 400 in sliding relationship. A link 232 connects each limiter 230 to the housing 200. The links 232 independently move each limiter 230 to reposition it relative to the pins 400. Thus, the pins 400 can be limited to any desired pattern of pin projection. Alternatively the links 232 may be connected directly to the pins 400.

In another alternative arrangement, the pins 400 themselves are made of a shape memory alloy. Each pin 400 is connected to an electrical circuit such that an electrical current can be sent to the pin 400 to cause the pin 400 to change length. The current to each pin 400 is controlled by a second control signal from the surgical navigation system, separate from the first control signal that drives the pins 400, to produce a desired pin length. While the drive mechanism 300 reciprocates the pins 400, electrical current is selectively applied to each pin to vary its length and therefore its projection distance.

Figures 6, 7, 8:
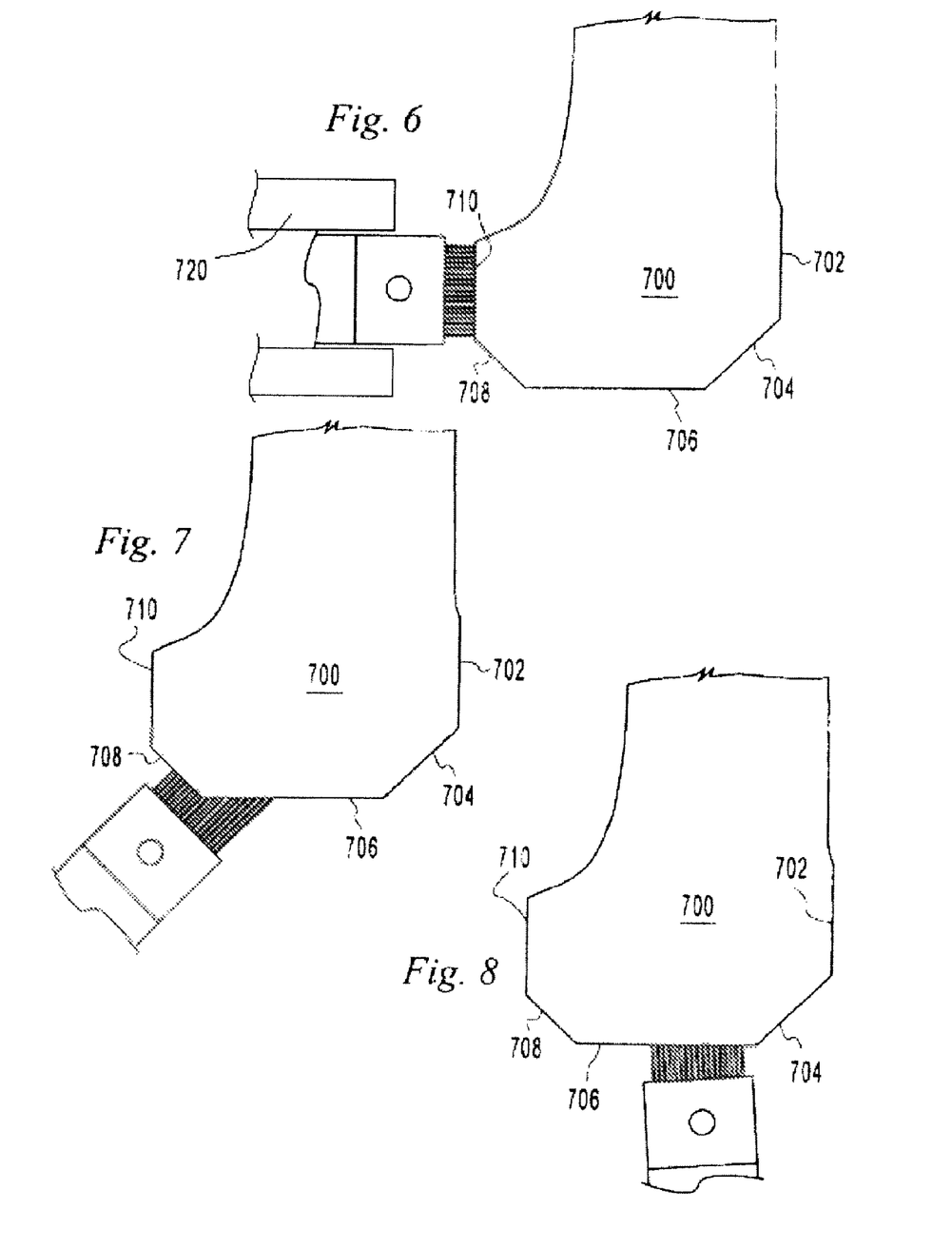
FIGS. 6-8 are side elevation views of the instrument of FIG. 1 in use to prepare a bone during surgery.

FIGS. 6-8 illustrate the use of the illustrative pin driver 100 to prepare a distal femur 700 for receiving a femoral component of a total knee implant. In a typical total knee surgery, the distal femur 700 is prepared by cutting the bone to produce five planar surfaces including an anterior surface 702, an anterior chamfer surface 704, a distal surface 706, a posterior chamfer surface 708, and a posterior surface 710. The pin driver 100 can be held in precise alignment with the bone 700 as in FIG. 6 and activated to form the posterior planar surface 710, for example. The alignment can be facilitated by using a cut guide 720 as is known in the art. However, by using a surgical navigation system to control the pins 400, the pin driver 100 can be positioned roughly by hand adjacent the bone 700 and the system will drive the appropriate pins to the appropriate depth to produce the desired shape as shown in FIGS. 7 and 8. In FIG. 7, the pin driver 100 is at the transition between two surfaces 706, 708. The pins are driven to only impact bone that is in the impact-zone to produce the desired shape. In FIG. 8, the pin driver 100 is angled relative to the desired cut, but the pins are selectively driven to produce the planar surface 706 at the desired orientation. By passing the pin driver 100 back-and-forth over the bone 700, a precise shape will be chiseled into the end of the bone without the user having to be aware of the pin 400 positions at any given moment.

Alternatively, the pin driver may be used to abrade and/or perforate bone without changing the gross shape of the bone. For example, one or more of the planar cuts 702, 704, 706, 708, 710 may be made with conventional instruments, such as a saw blade and guide. The pin driver 100 may then be passed over the surface to perforate the bone and create a texture for improved interdigitation with bone cement. Similarly, the pin driver 100, with the appropriate configuration of pin geometry and drive parameters, may be passed over the surface of a bone to compact the bone into a more dense form. Similarly, the pin driver 100 may be passed over the surface of a bone to produce a recognizable mark-for later reference. Texturing without changing the gross surface shape may be accomplished by increasing the pin 400 spacing, reducing the pin 400 firing frequency, reducing the pin 400 size, increasing pin 400 sharpness, reducing the time the pin driver 100 is applied to the bone, and/or other suitable methods that retain a structurally sound portion of the bone surface surrounding the perforations created by the pin driver. Compacting bone may be facilitated by increasing pin 400 size, blunting the pin 400 tips, and/or other suitable methods. Marking bone may be facilitated in similar ways and by firing the pins in sequential manner and/or in defined patterns to produce recognizable marks on the bone.

Figure 9:
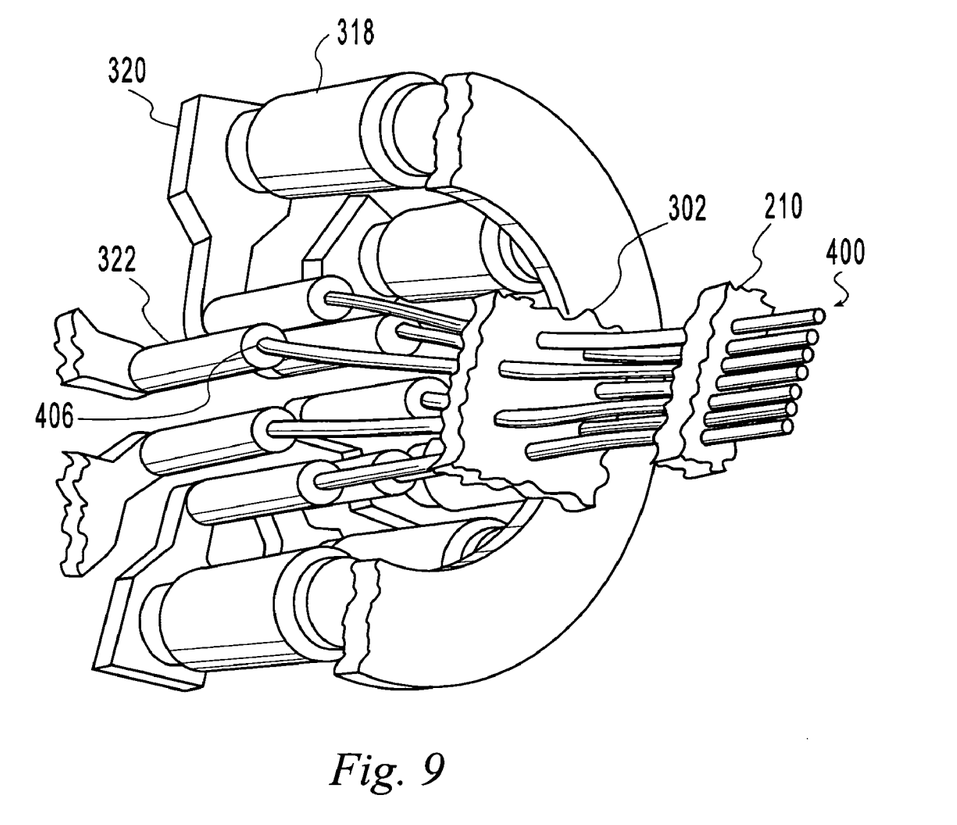
FIG. 9 is a schematic view of an exemplary drive mechanism for the instrument of FIG. 1.

FIG. 9 illustrates one exemplary drive mechanism. The drive mechanism includes an electromagnet 318, armature 320, and hammer 322 associated with each pin 400. The armatures 320 are pivoted within the drive mechanism 300 and the hammers 322 are attached to each armature 320. The pins 400 are slidingly received through the pin guide 210 and through the proximal face 302 of the drive mechanism. The distal end 406 of each pin is positioned adjacent its corresponding hammer 322. The pins 400 may optionally be attached to the hammers 322. When a particular pin is to be fired, a control signal is sent from the control unit 600 to the corresponding electromagnet 318. As the electromagnet 318 is energized, it pivots the armature 320 and hammer 322 toward the pin 400 causing the hammer 322 to drive the pin. The force and/or distance of the pin activation may be controlled by varying the amplitude and/or duration of the control signal to thereby vary the strength and time of influence of the electromagnet. Alternatively, the depth limiters of FIGS. 4 and 5 may be used with the drive mechanism of FIG. 9.

Although examples of a pin driver and its use have been described and illustrated in detail, it is to be understood that the same is intended by way of illustration and example only and is not to be taken by way of limitation. The invention has been illustrated in use to prepare a distal femur to receive a femoral component of a total knee prosthesis in knee replacement surgery. However, the pin driver may be used at other locations within a patient's body to remove and/or abrade bone for other purposes. Accordingly, variations in and modifications to the pin driver and its use will be apparent to those of ordinary skill in the art, and the following claims are intended to cover all such modifications and equivalents.

What is claimed is:

1. An orthopaedic pin driver for impacting bone at a surgical site, the pin driver comprising:
   a housing having a proximal end, a distal end, and a longitudinal axis therebetween;
   an array of pins mounted in the housing for reciprocating motion parallel to the longitudinal axis between a first longitudinal position and a second longitudinal position, each pin having a proximal end and a distal end, the proximal end of each pin forming a sharpened tip projecting from the housing by a projection distance at least when each pin is in the second longitudinal position, the array of pins arranged in a two-dimensional pattern to be reproduced on a surface of the bone by an impacting action of the pins;
   a drive mechanism engaging the pins to reciprocate the pins between the first and second positions, the drive mechanism selectively driving individual pins of the array of pins in response to a control signal, the array of pins arranged in an array of columns and rows, the drive mechanism being able to selectively drive individual pins in the array to produce a variety of user selectable patterns; and
   a limiting means for individually limiting travel of the pins reciprocating between the first and second positions and for individually varying a maximum projection distance of each pin.

2. The pin driver of claim 1 wherein the drive mechanism is controllable to vary the force with which individual pins of the array of pins are driven.

3. The pin driver of claim 1 wherein the drive mechanism is controllable to vary the distance individual pins of the array of pins are driven.

4. The pin driver of claim 1 wherein the drive mechanism is controllable to vary the inertia of the pins of the array of pins.

5. The pin driver of claim 1 wherein the limiting means comprises a plate including a plurality of holes, each hole receiving a pin and each pin including a projection abuttable with the plate, the pin driver further comprising an actuator connected to the plate to vary the position of the plate relative to the housing.

6. The pin driver of claim 1 further comprising an actuator connected to the limiting means to control the position of the limiting means relative to the at least one pin and housing.

7. The pin driver of claim 6 wherein the actuator is controlled by an input signal.

8. The pin driver of claim 1 wherein the drive mechanism is controlled by a first input signal and the limiting means is controlled by a second input signal, the first and second input signals being coordinated by a computer to produce a desired effect on the bone.

9. The pin driver of claim 1 further comprising a shape memory alloy link linking the limiting means to the housing, the link changing shape under control input to vary the position of the limiting means.

10. The pin driver of claim 1, wherein the limiting means comprises a plurality of limiters, each limiter engaging a pin of the array of pins to limit the pin's projection distance, each limiter being individually controllable to individually limit its corresponding pin's projection distance.

11. The pin driver of claim 10 wherein each limiter includes a link that changes length in response to a control input.

12. The pin driver of claim 1 wherein at least one pin of the array of pins is responsive to a control input to change length to vary the at least one pin's projection distance.

13. The pin driver of claim 12 wherein the drive mechanism is controlled by a first input signal and the at least one pin's length is controlled by a second input signal.

14. The pin driver of claim 1 further comprising a separate cut guide positionable at a surgical site, the housing being engageable with the cut guide to position the array of pins relative to the surgical site.

15. The pin driver of claim 1 wherein the drive mechanism comprises a hammer and an electromagnet associated with each pin, the hammer moving under influence of the electromagnet to drive the pin.

16. The pin driver of claim 1 further comprising a conduit extending longitudinally from the proximal end of the housing to the distal end of the housing to conduct debris away from the surgical site.

17. The pin driver of claim 1 further comprising a tracking element detectable by a surgical navigation system to guide the positioning of the pin driver.

18. The pin driver of claim 1 further comprising:
a surgical navigation system including a surgical navigation coordinate system, the surgical navigation system able to output the control signal to control the drive mechanism;
a tracking element mounted to the housing, the tracking element being detectable by the surgical navigation system to indicate the position of the pins within the surgical navigation system, the surgical navigation system outputting a first control signal to control the drive mechanism to reciprocate the pins when the pins are positioned in a desired relationship to the bone.

19. The pin driver of claim 18 wherein the limiting means engages at least one pin of the array of pins to limit a parameter of the at least one pin's reciprocation, the surgical navigation system outputting a second control signal to control the limiting means, the parameter of the at least one pin's reciprocation being selected from the parameters consisting of projection length, reciprocation force, reciprocation speed, and reciprocation inertia.

20. The pin driver of claim 1 wherein the pins are each sharpened to a conical point.

21. The pin driver of claim 1 wherein the pins are each sharpened to a chisel point.

22. The pin driver of claim 1 wherein each pin is hollow.

23. The pin driver of claim 22 wherein each pin defines a sharp cutting rim at its proximal end.

24. The pin driver of claim 5 wherein the plate is able to be angled relative to the housing to limit the projection distances of the array of pins to an angled projection plane.

25. The pin driver of claim 6 wherein the actuator is manually activated.

26. The pin driver of claim 7 wherein the actuator is computer controlled.

27. The pin driver of claim 11 wherein the link comprises a shape memory alloy.

28. The pin driver of claim 12 wherein the at least one pin comprises a shape memory alloy.

29. The pin driver of claim 28 wherein the shape memory alloy is responsive to an electrical current to change length.

30. The pin driver of claim 15 wherein the movement of each pin is adjustable by varying the control signal sent to the electromagnet.

31. An orthopaedic pin driver for impacting bone at a surgical site, the pin driver comprising:
a housing having a proximal end, a distal end, and a longitudinal axis therebetween;
an array of pins mounted in the housing for reciprocating motion parallel to the longitudinal axis between a first longitudinal position and a second longitudinal position, each pin having a proximal end and a distal end, the proximal end of each pin forming a sharpened tip projecting from the housing by a projection distance at least when each pin is in the second longitudinal position, the array of pins arranged in a two-dimensional pattern to be reproduced on a surface of the bone by an impacting action of the pins;
a drive mechanism engaging the pins to reciprocate the pins between the first and second positions, the array of pins arranged in an array of columns and rows, the drive mechanism being able to selectively drive individual pins in the array to produce a variety of user selectable patterns; and
a plurality of barriers engaging at least one pin of the array of pins, each barrier individually limiting travel of the at least one pin reciprocating between the first and second positions and individually varying a maximum projection distance of each pin.

32. The pin driver of claim 31 wherein the drive mechanism is controllable to vary one or more of the following: a force with which individual pins of the array of pins are driven, a distance individual pins of the array of pins are driven, and an inertia of the pins of the array of pins.

33. The pin driver of claim 31 further comprising an actuator connected to the limiting means to control the position of the limiting means relative to the at least one pin and housing, wherein the actuator is controlled by an input signal.

34. The pin driver of claim 31 wherein at least one pin of the array of pins is responsive to a control input to change length to vary the at least one pin's projection distance, wherein the at least one pin comprises a shape memory alloy responsive to an electrical current to change length.

35. The pin driver of claim 31 further comprising a separate cut guide positionable at a surgical site, the housing being engageable with the cut guide to position the array of pins relative to the surgical site.

36. The pin driver of claim 31 further comprising a conduit extending longitudinally from the proximal end of the housing to the distal end of the housing to conduct debris away from the surgical site.

37. The pin driver of claim 31 further comprising:

a surgical navigation system including a surgical navigation coordinate system, the surgical navigation system able to output the control signal to control the drive mechanism;

a tracking element mounted to the housing, the tracking element being detectable by the surgical navigation system to indicate the position of the pins within the surgical navigation system, the surgical navigation system outputting a first control signal to control the drive mechanism to reciprocate the pins when the pins are positioned in a desired relationship to the bone, wherein at least one of the plurality of barriers engages at least one pin of the array of pins to limit a parameter of the at least one pin's reciprocation, the surgical navigation system outputting a second control signal to control the plurality of barriers, the parameter of the at least one pin's reciprocation being selected from the parameters consisting of projection length, reciprocation force, reciprocation speed, and reciprocation inertia.

38. The pin driver of claim 31 wherein the drive mechanism comprises a hammer and an electromagnet associated with each pin, the hammer moving under influence of the electromagnet to drive the pin, wherein the movement of each pin is adjustable by varying the control signal sent to the electromagnet.

* * * * *